United States Patent [19]

Speranza et al.

[11] Patent Number: 5,139,706
[45] Date of Patent: Aug. 18, 1992

[54] FATTY AMIDES PREPARED BY REACTING DICARBOXYLIC ACIDS, POLYOXYALKYLENE AMINE BOTTOMS PRODUCTS AND FATTY ACIDS OR ESTERS THEREOF

[75] Inventors: George P. Speranza; Wei-Yang Su, both of Austin, Tex.

[73] Assignee: Texaco Chemical Company, White Plains, N.Y.

[21] Appl. No.: 653,932

[22] Filed: Feb. 12, 1991

Related U.S. Application Data

[63] Continuation of Ser. No. 522,770, May 14, 1990, abandoned.

[51] Int. Cl.$^5$ .......................... C11D 1/72; C11D 3/32; C11D 13/14; C07C 231/02
[52] U.S. Cl. ...................... 252/548; 252/174; 252/174.21; 252/DIG. 16; 564/138; 564/160
[58] Field of Search ............. 252/544, 117, DIG. 16, 252/174.21, 174, 548; 564/138, 160

[56] References Cited

U.S. PATENT DOCUMENTS

| | | | |
|---|---|---|---|
| 3,043,778 | 7/1962 | Kelly | 252/107 |
| 3,383,320 | 5/1968 | Bell, Jr. | 252/132 |
| 3,563,902 | 2/1971 | Schmadel et al. | 252/152 |
| 3,625,903 | 12/1971 | Davies | 252/107 |
| 3,654,167 | 4/1972 | Akrongold et al. | 252/119 |
| 3,663,444 | 5/1972 | Schmadel | 252/99 |
| 3,882,090 | 5/1975 | Fagerburg et al. | 260/78 R |
| 4,201,743 | 5/1980 | Perla et al. | 264/148 |
| 4,438,010 | 5/1984 | Lindauer et al. | 252/91 |
| 4,453,909 | 6/1984 | Lindauer et al. | 425/511 |
| 4,515,707 | 5/1985 | Brooks | 252/368 |
| 4,521,541 | 6/1985 | Rutherford | 521/79 |
| 4,735,746 | 4/1988 | Speranza et al. | 252/544 |
| 4,795,581 | 1/1989 | Nieh et al. | 252/77 |
| 4,828,757 | 5/1989 | Naylor et al. | 252/544 |
| 4,946,618 | 8/1990 | Knochel et al. | 252/117 |

*Primary Examiner*—Paul Lieberman
*Assistant Examiner*—Erin M. Higgins
*Attorney, Agent, or Firm*—Jack H. Park; Kenneth R. Priem; David L. Mossman

[57] ABSTRACT

Surfactant composition prepared by reacting dicarboxylic acids and esters thereof, such as adipic acid, diethyl oxalate, etc.; a polyoxyalkyleneamine residue, such as an alkylene glycol diamine bottoms product, and fatty acids and esters thereof, such as tallow acid or coconut acid, are described. These nonionic surfactant compositions are useful for preparing surfactant bars, or other molded or shaped articles such as toys.

40 Claims, No Drawings

FATTY AMIDES PREPARED BY REACTING DICARBOXYLIC ACIDS, POLYOXYALKYLENE AMINE BOTTOMS PRODUCTS AND FATTY ACIDS OR ESTERS THEREOF

CROSS-REFERENCE TO RELATED APPLICATION

This application is a continuation-in-part of application Ser. No. 07/522,770, filed May 14, 1990, abandoned.

BACKGROUND OF THE INVENTION

1. Field of the Invention

This invention relates to surfactant compositions. More particularly, this invention relates to fatty acid amide surfactant compositions prepared by reacting polyoxyalkyeneamine residues or bottoms products with dicarboxylic acids and esters thereof and fatty acids and esters thereof. The solid products of this invention can be shaped or molded as surfactant bars, toys or other useful articles.

Triethylene and tetraethylene glycol diamines may be continuously produced from glycols catalytically. The triethylene glycol diamine and tetraethylene glycol diamine products are known under the trade names JEFFAMINE® EDR-148 amine and JEFFAMINE® EDR-192 amine, respectively, as made by Texaco Chemical Co. These materials are useful as intermediates in the preparation of hydrophilic nylon resins, and as epoxy curing agents. However, in the production of polyethylene glycol diamine, there are also produced significant quantities of bottoms products or residues, and it would be beneficial if uses for these materials could be discovered.

2. Prior Art

Surfactant compositions, either in liquid or solid form, have long been used for washing the human body, laundering clothing, cleaning kitchenware, and for a variety of other cleaning operations. Solid surfactant compositions in the form of solid bars represent a convenient means of dispensing a surface active agent at the point of use. Solid bars having additional components therein, such as abrasives, etc., to enhance the cleaning qualities of the bar, are described in the art.

U.S. Pat. No. 3,383,320 describes a detergent bar consisting of a solid, water-soluble detergent such as a condensation product of an epoxide such as ethylene oxide with a fatty acid or fatty acid amide held in a solid matrix of a sintered thermoplastic resin such as polypropylene.

U.S. Pat. No. 3,663,444 describes a washing composition consisting essentially of a surface-active detergent composition and from 0.1 to 20 percent of a water-soluble polyamide reaction product of a polyalkyleneamine and a polycarboxylic acid having 2 to 10 carbon atoms such as oxalic acid, etc.

U.S. Pat. No. 3,563,902 describes a detergent composition containing 0.1 to 20 weight percent of a water-soluble salt of a free carboxyl group containing polyamide where the acid and amide radicals, respectively, are derived from tricarboxylic and tetracarboxylic acids and diamines.

U.S. Pat. No. 3,882,090 describes water-soluble polyamides having ether linkages in the polymer chain comprised of (A) an aliphatic dicarboxylic acid such as adipic acid, (B) up to about 25 mole percent of a nine carbon aliphatic dicarboxylic acid, and (C) an (alkyleneoxy) bis (propylamine). These polyamides are useful as sizing agents, coatings and adhesives.

U.S. Pat. No. 4,735,746 describes a detergent bar consisting of 5 to 95 weight percent of a water-soluble polyamide or polyester with a surface active agent as a major portion of the balance. Polyamides prepared from an acid, such as adipic or glutaric acid, and a diamine, such as an alkylene glycol diamine, are disclosed.

U.S. Pat. No. 3,654,167 describes a washing polymer prepared by mixing, while heating, a polymeric fat acid polyamide and a fatty acid compound such as the diethanolamide of a fatty acid. These soluble washing polymers can be readily used in the form of washing bars, soft gels, etc.

SUMMARY OF THE INVENTION

This invention relates to water-soluble surfactant compositions, including surfactant bars, which are fatty acid amide surfactant compositions and to processes for preparing such surfactants. The processes employed to prepare the surfactant compositions comprise reacting at least one polyoxyalkyleneamine residue, such as triethylene glycol diamine bottoms products, further aminated triethylene glycol diamine bottoms products, tetraethylene glycol diamine bottoms products, and further aminated tetraethylene glycol diamine bottoms products, at least one compound selected from the group consisting of dicarboxylic acids and dicarboxylic acid esters and at least one component selected from the group consisting of fatty acids and fatty acid esters.

In the two-step process for preparing the surfactant compositions of this invention, at least one dicarboxylic acid or dicarboxylic acid ester is reacted with at least one polyoxyalkyleneamine residue to form the condensation product thereof which is subsequently reacted with a fatty acid or fatty acid ester. In another embodiment of this invention, the three ingredients, namely the dicarboxylic acid or ester, the polyoxyalkyleneamine residue and the fatty acid or ester are charged together to a reactor and the product formed in a one-step operation.

DESCRIPTION OF THE PREFERRED EMBODIMENTS

It has been discovered that valuable fatty acid amide surfactants or soaps can be prepared by the reaction of dicarboxylic acids, such as adipic acid, glutaric acid, etc. and esters thereof, with polyoxyalkyleneamine residues and fatty acids and esters thereof, such as tallow acid, coconut acid, etc. The solid, water-soluble products of this invention, which range from hard soaps to soft, waxy products, can be molded or shaped into detergent bars, toys and other articles.

The polyoxyalkylene residues used to make the novel fatty acid amide surfactants may be residues, bottom products or further aminated bottoms products such as from the JEFFAMINE® EDR amines process and may contain mixtures of triethylene glycol monoamine, triethylene glycol diamine, tetraethylene glycol monoamine, triethylene glycol diamine, tetraethylene glycol mono and diamines and condensation products from the process. In this way, otherwise undesirable bottoms products may be usefully employed in preparing the products of this invention.

It will be appreciated that the reaction products of this invention, i.e., the fatty acid amide surfactants, will be complex mixtures. Although the products are complex mixtures, they represent valuable surfactant compositions which are useful in preparing nonionic surfactant bars and in other surfactant applications.

Dicarboxylic acids and esters useful in the process of this invention include compounds of the formula:

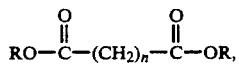

wherein R is hydrogen or alkyl of from 1 to 5 carbon atoms and n ranges from 0–8 as exemplified by oxalic, malonic, succinic, glutaric and adipic acids and by diethyl oxalate, dipropyl oxalate, dimethyl malonate, diethyl adipate, dimethyl glutarate, etc.

Fatty acids suitable for preparing the nonionic surfactant compositions of this invention may be defined as RCOOH, where R is a linear or branched alkyl, alicyclic or alkylene group of from about 7 to 23 carbon atoms, and in a narrower aspect from about 11 to 17 carbon atoms. The suitable fatty acid esters have structures of RCOOR' where R and R' are alkyl groups having a R+R' sum of carbon atoms within the ranges set out above. The fatty acids and esters may be cyclic as well. Useful fatty acids include capric, caprylic, lauric, myristic, palmitic, stearic, oleic, linolenic, etc. and mixtures thereof. Suitable fatty acid esters include, for example, palm oil, coconut oil, soybean oil and tallow.

Preferred polyoxyalkyleneamine resides for use in preparing the products of this invention include bottoms products resulting from the manufacture of JEFFAMINE ® EDR amines as exemplified by triethylene glycol diamine and tetraethylene glycol diamines, known under the trade names JEFFAMINE ® EDR-148 amine and JEFFAMINE ® EDR-192 amine, respectively. The numbers refer to the approximate molecular weight. These compounds have the following respective structures:

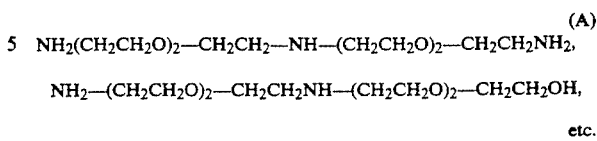

While the residues or bottoms products from these processes have not been completely identified, they are known in the case of bottoms products from the triethylene glycol diamine process (i.e., JEFFAMINE ® EDR-148 amine bottoms products) to contain mixtures of triethylene glycol mono- and diamines, and condensation products, such as:

$$NH_2(CH_2CH_2O)_2-CH_2CH_2-NH-(CH_2CH_2O)_2-CH_2CH_2NH_2, \quad (A)$$

$$NH_2-(CH_2CH_2O)_2-CH_2CH_2NH-(CH_2CH_2O)_2-CH_2CH_2OH,$$

etc.

with the principal product being the diamine (A). Similar compounds are found in the bottoms products from the tetraethylene glycol diamine process (i.e., JEFFAMINE ® EDR-148 amine bottoms products).

Further aminated triethylene glycol diamine bottoms products and tetraethylene glycol bottoms products may also be employed in preparing the fatty acid amide surfactant products of this invention. Such further aminated bottoms products are prepared by subjecting the triethylene glycol diamine bottoms products or tetraethylene glycol diamine bottoms products to a second amination step conducted in the presence of ammonia and hydrogen and with the aid of a catalyst. In this amination operation additional hydroxyl groups of compounds included in the bottoms products are converted to amino groups.

When preparing the fatty acid amide surfactant compositions of this invention using the two-step process, the reaction of the major component of further aminated JEFFAMINE ® EDR-148 amine bottoms products with, for example, adipic acid and lauric acid may be represented as follows:

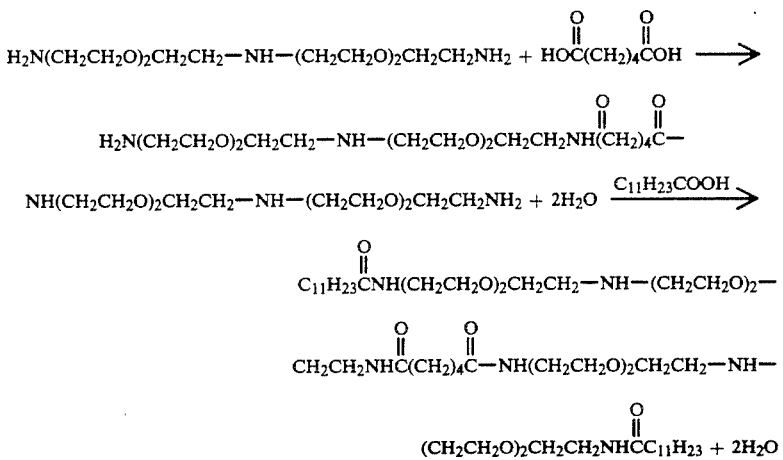

Bottoms products from any process will vary somewhat, and are thus difficult to define with precision. The bottoms products from the JEFFAMINE ® EDR process will vary depending on the temperature and pressure which they are subjected to. Although one aspect of this invention contemplates the use of JEFFAMINE ® EDR amine residues, the invention is not limited to the use of such particular residues, but may apply to any amine residues or bottoms products or mixtures thereof, or even mixture of residues with relatively more pure amine, regardless of whether or not they are exemplified by structure or name herein, that fall within the claimed definitions.

The process employed to make the fatty acid amide surfactants of this invention may be performed simply and easily. For both steps of the two-step process and for the one-step process of this invention the reaction temperature ranges from about 100° to about 250° C. while pressures may range from atmospheric to 200 psig, although reduced pressures may also be used. Water formed as the reaction proceeds is removed from the reaction mixture.

In one embodiment of the invention the proportion of the dicarboxylic acid compound ranges from about 5 to about 30 percent by weight based on the weight of the polyoxyalkyleneamine residue and the fatty acid component ranges from about 20 to about 85 percent by weight based on the weight of the polyoxyalkyleneamine residue.

The fatty acid amide surfactant compositions of the instant invention may also include builders, brighteners, hydrotropes, germicides, soil-suspending agents, antioxidants, bleaches, coloring materials, perfumes, water-soluble alcohols, foam boosters, abrasives, etc.

The preparation of solid bars from the compositions of this invention is well within the capability of persons of ordinary skill in the art of forming bars of toilet soap. The surfactant bars described herein are manufactured by mixing the raw materials into a homogeneous mass and molding, extruding, cutting and stamping the mass to form uniform bars or cakes.

Methods for the manufacture of surfactant bars from solid surfactant compositions such as those of the instant invention, are well known in the art and are described in U.S. Pat. Nos. 4,201,743, 4,453,909, 4,438,010, 4,515,707 and 4,521,541.

The following examples illustrate various embodiments of the instant invention but are not intended to be limitative.

EXAMPLE 1

Surfactant Composition from Further Aminated JEFFAMINE ® EDR-148 Amine Bottoms Product, Adipic Acid and Tallow Acid The further aminated bottoms product (Product 6654-16-1) utilized in this example was prepared by subjecting a final still bottoms product from the EDR-148 amine process (Product FA-9) to an additional amination step conducted by reacting the bottoms product with ammonia in the presence of hydrogen and with the aid of a catalyst. The analysis of Products FA-9 and 6654-16-1 are shown in Table 1.

To a one liter three-necked flask equipped with a thermometer, Dean-Stark trap, stirrer, and nitrogen inlet were charged 300 g of further aminated JEFFAMINE ® EDR-148 amine bottoms (Product 6454-16-1) and 65.3 g of adipic acid. The mixture was heated at 220° for two hours. The reaction mixture was cooled, 246.2 g of tallow acid was added and heating was continued at 220° C. for two hours. Water generated was removed through the Dean-Stark trap. The resulting product (6477-42) (573.6 g), a yellow, water-soluble solid (m.p. 84°-85° C.), had the following analysis:

| Total Acetylatables | 113 mg KOH/g |
| Acid Value | 1.91 mg KOH/g |
| Total Amine | 1.760 meq/g |
| Primary Amine | 0.163 meq/g |
| Tertiary Amine | 0.076 meq/g |

On shaking in 25 ml of water, a 0.5 g sample dissolved slowly to form a soapy solution.

TABLE 1

| Bottoms Products Characterizations | | |
|---|---|---|
| | EDR-148 Bottoms (Product FA-9) | Further Aminated EDR-148 Bottoms Product (Product 6454-16-1) |
| Total Acetylatables | 9.510 meq/g | 9.839 meq/g |
| Total Amine | 7.901 meq/g | 9.377 meq/g |
| Primary Amine | 4.066 meq/g | 5.966 meq/g |
| Secondary Amine | 3.747 meq/g | 3.296 meq/g |
| Tertiary Amine | 0.088 meq/g | 0.115 meq/g |

EXAMPLE 2

Surfactant Composition from Further Aminated JEFFAMINE ® EDR-148 Amine Bottoms Product, Adipic Acid and Coconut Acid The procedure of Example 1 was followed except that 190.7 g of coconut acid, 65.3 g of adipic acid, and 300 g of further aminated JEFFAMINE ® EDR-148 amine bottoms (6454-16-1) were used. The resulting product (6477-54) (552 g), a yellow solid (m.p. 76°-78° C.), had the following analysis:

| Total Acetylatables | 124 mg KOH/g |
| Acid Value | 3.33 mg KOH/g |
| Total Amine | 2.011 meq/g |
| Primary Amine | 0.216 meq/g |
| Tertiary Amine | 0.070 meq/g |

On shaking in 25 ml of water, a 0.5 g sample dissolved easily to give a soapy solution.

EXAMPLE 3 (COMPARATIVE)

Reaction Product from JEFFAMINE ® EDR-148 Amine, Adipic Acid and Tallow Acid

To a one liter three-necked flask equipped with a stirrer, thermometer, Dean-Stark trap, and nitrogen inlet were charged 148 g of JEFFAMINE ® EDR-148 amine and 73 g of adipic acid. The mixture was heated at 180° C. for two hours. The reaction mixture was cooled and 275 g of tallow acid was added following which the mixture was heated at 240° C. for two hours. Water generated was removed through the Dean-Stark trap. The resulting product (6469-40) (440.9 g) was not water soluble.

EXAMPLE 4 (COMPARATIVE)

Reaction Product from JEFFAMINE ® EDR-192 Amine, Adipic Acid and Coconut Acid

The procedure of Example 3 was followed except that 192 g of JEFFAMINE ® EDR-192 amine, 73 g of adipic acid and 213 g of coconut acid were used. The resulting product was not water soluble.

EXAMPLE 5

Surfactant Composition from Further Aminated JEFFAMINE ® EDR-148 Amine Bottoms Product, Glutaric Acid and Tallow Acid The further aminated JEFFAMINE ® EDR-148 amine bottoms product utilized in this example (i.e., Product 6454-17-1) had the following properties:

| Total Acetylatables | 10.0 meq/g |
| Total Amine | 9.302 meq/g |
| Primary Amine | 5.797 meq/g |

| | |
|---|---|
| Secondary Amine | 3.415 meq/g |
| Tertiary Amine | 0.090 meq/g |

To a 500 ml three-necked flask equipped with a thermometer, Dean-Stark trap, stirrer, and nitrogen inlet 172.5 g of further aminated JEFFAMINE ® EDR-148 amine bottoms (Product 6454-17-1) and 33 g of glutaric acid were charged. The mixture was heated to 220° C. and held at that temperature until no additional water came off. The reaction mixture was cooled to about 150° C., 137.5 g of tallow acid added and the mixture heated to 220° C. The reaction mixture was held at 220° C. for 30 minutes after no more water came off. The resulting product (6469-90) (322.9 g), a light tan solid (m.p. 43°–44° C.), had the following analysis:

| | |
|---|---|
| Acid Value | 4.38 mg KOH/g |
| Total Amine | 1.903 meq/g |
| Primary Amine | 0.210 meq/g |
| Tertiary Amine | 0.060 meq/g |

On shaking in 25 ml of water, a 0.5 g sample dissolved with difficulty to give a soapy solution.

EXAMPLE 6

Surfactant Composition from Further Aminated JEFFAMINE ® EDR-148 Amine Bottoms Product, Glutaric Acid and Coconut Acid The procedure of Example 5 was followed except that 172.5 g of further aminated JEFFAMINE ® EDR-148 amine bottoms (Product 6454-17-1), 33 g of glutaric acid, and 106.5 g of coconut acid were used. The resulting product (6469-91), an ivory-like solid (m.p. 74°–80° C.), had the following analysis:

| | |
|---|---|
| Acid Value | 2.31 mg KOH/g |
| Total Amine | 2.127 meq/g |
| Tertiary Amine | 0.070 meq/g |
| Primary Amine | 0.242 meq/g |

On shaking in 25 ml of water, a 0.05 g sample dispersed well and exhibited good sudsing action.

EXAMPLE 7

Surfactant Composition from Further Aminated JEFFAMINE ® EDR-148 Amine Bottoms Product, Diethyl Oxalate and Tallow Acid The procedure of Example 5 was followed except that 172.5 g further aminated JEFFAMINE ® EDR-148 amine bottoms (Product 6454-17-1), 36.5 g of diethyl oxalate and 137.5 g of tallow acid were used. The resulting product (6469-93) (312.1 g), a light tan solid (m.p. 58°–60° C.), had the following analysis:

| | |
|---|---|
| Acid Value | 5.17 mg KOH/g |
| Total Amine | 1.977 meq/g |
| Tertiary Amine | 0.052 meq/g |
| Primary Amine | 0.251 meq/g |

On shaking in 25 ml of water, a 0.5 g sample yielded a turbid soapy solution.

EXAMPLE 8

Surfactant Composition from JEFFAMINE ® EDR-148 Amine Bottoms Product, Adipic Acid and Coconut Acid To a 500-ml three-necked flask equipped with a thermometer, stirrer, Dean-Stark trap, and nitrogen outlet was charged 123 g of JEFFAMINE ® EDR-148 amine bottoms (Product FA-9), 18.2 g of adipic acid, and 53 g of coconut acid. The mixture was heated to 230° C. and held for one hour after no additional water came off. The resulting product (6469-96) (180.2 g) was a brown wax which had the following analysis:

| | |
|---|---|
| Acid Value | 4.20 mg KOH/g |
| Total Amine | 2.086 meq/g |
| Primary Amine | 0.214 meq/g |

On shaking in 25 ml of water, a 0.5 g sample dissolved at a rapid rate and exhibited good foaming properties.

EXAMPLE 9

Surfactant Composition from JEFFAMINE ® EDR-148 Amine Bottoms Product, Adipic Acid and Tallow Acid The procedure of Example 8 was followed except that 69 g of tallow acid, 18.2 g of adipic acid, and 123 g of JEFFAMINE ® EDR-148 amine bottoms (Product FA-9 bottoms) were used. The resulting product (6469-97) (196.8 g), a brown wax, had the following analysis:

| | |
|---|---|
| Acid Value | 2.09 mg KOH/g |
| Total Amine | 1.892 meq/g |
| Primary Amine | 0.186 meq/g |

On shaking in 25 ml of water, a 0.5 g sample was slow to dissolve, but gave a reasonably good foamer.

EXAMPLE 10

Surfactant Composition from JEFFAMINE ® EDR-192 Amine Bottoms Product, Adipic Acid and Tallow Acid The EDR-192 amine bottoms (6254-20-28) utilized in this example and in Example 12 which follows had the following properties:

| | |
|---|---|
| Total Acetylatables | 11.1 meq/g |
| Total Amine | 3.85 meq/g |
| Primary Amine | 2.21 meq/g |
| Secondary Amine | 1.30 meq/g |
| Tertiary Amine | 0.34 meq/g |

To a 500 ml three-necked flask equipped as in Example 5 were added 69 g of tallow acid, 18.2 g of adipic acid and 226.3 g of EDR-192 amine bottoms. The contents were heated to 230° C. and held at this temperature for about three hours during which time about 7.9 ml of water was collected.

A sample (0.5 g) was dissolved in 25 ml of water. The solution formed an excellent thick foam.

The product (6469-98) had the following analysis:

| | |
|---|---|
| Acid Value | 3.40 mg KOH/g |

| | |
|---|---|
| Total Amine | 1.330 meq/g |
| Primary Amine | 0.316 meq/g |

EXAMPLE 11

Surfactant Composition from JEFFAMINE® EDR-192 Amine Bottoms Product, Adipic Acid and Coconut Acid Example 10 was repeated except that 53 g of coconut acid, 18.2 g of adipic acid, and 226.3 g of EDR-192 amine bottoms were used (6254-20-28). About 7.7 ml of water was collected overhead.

On shaking in 25 ml of water at 0.5 g, sample of the product (6469-99) dissolved readily yielding an excellent foam. The product was employed to cleanse laboratory glassware.

The product analyzed as follows:

| | |
|---|---|
| Acid Value | 2.23 mg KOH/g |
| Total Amine | 1.442 meq/g |
| Primary Amine | 0.556 meq/g |

EXAMPLE 12

Surfactant Composition from Further Aminated JEFFAMINE® EDR-148 Amine Bottoms, Adipic Acid and Coconut Acid To a one liter three-necked flask equipped with a thermometer, Dean-Stark trap, stirrer, and nitrogen inlet were charged 345 g of further aminated JEFFAMINE® EDR-148 amine bottoms (6454-16), 73 g of adipic acid, and 213 g of coconut acid. The mixture was heated at 230° C. for two hours and water generated was removed through the Dean-Stark trap. The resulting product (6477-66) (594.4 g) a light yellow solid (m.p. 74°-78° C.), had the following analysis:

| | |
|---|---|
| Total Acetylatables | 132 mg KOH/g |
| Acid Value | 6.03 mg KOH/g |
| Total Amine | 1.992 meq/g |
| Primary Amine | 0.298 meq/g |
| Tertiary Amine | 0.062 meq/g |

On shaking with 25 ml of water, a 0.5 g sample dissolved readily with nice sudsing action.

What is claimed is:

1. A water-soluble fatty acid amide surfactant composition prepared by reacting together at least one compound selected from the group consisting of dicarboxylic acids and esters thereof; at least one polyoxyalkyleneamine residue; and at least one component selected from the group consisting of fatty acids and esters thereof wherein the fatty acids and esters are selected from the formula consisting of RCOOH wherein R is a linear or branched alkyl, alicyclic or alkylene group of from about 7 to 23 carbon atoms and R'COOR" wherein R' and R" are alkyl groups having a R'+R" sum of from about 7 to 23 carbon atoms, and wherein the polyoxyalkyleneamine residue comprises at least one unreacted secondary amine —NH— moiety which exists following amide formation, wherein said compound ranges from about 5 to about 30 percent by weight based on the weight of the polyoxyalkyleneamine residue and said component ranges from about 20 to about 85 percent by weight based on the weight of the polyoxyalkyleneamine residue.

2. The fatty acid amide surfactant composition of claim 1 wherein the said polyoxyalkyleneamine residue is an alkylene glycol diamine bottoms product.

3. The fatty acid amide surfactant composition of claim 1 wherein the said polyoxyalkyleneamine residue is an ethylene glycol diamine bottoms product.

4. The fatty acid amide surfactant composition of claim 1 wherein the said polyoxyalkyleneamine residue is selected from the group consisting of triethylene glycol diamine bottoms products, further aminated triethylene glycol diamine bottoms products, tetraethylene glycol diamine bottoms products, further aminated tetraethylene glycol bottoms products, and mixtures thereof.

5. The fatty acid amide surfactant composition of claim 4 wherein the said polyoxyalkyleneamine residue is a triethylene glycol diamine bottoms product.

6. The fatty acid amide surfactant composition of claim 4 wherein the said polyoxyalkyleneamine residue is a further aminated triethylene glycol diamine bottoms product.

7. The fatty acid amide surfactant composition of claim 4 wherein the said polyoxyalkyleneamine residue is a tetraethylene glycol diamine bottoms product.

8. The fatty acid amide surfactant composition of claim 1 wherein the said polyoxyalkyleneamine residue is selected from the group consisting of triethylene glycol diamine bottoms products from the reductive amination of triethylene glycol, further aminated triethylene glycol diamine bottoms products from the reductive amination of triethylene glycol, tetraethylene glycol diamine bottoms products from the reductive amination of tetraethylene glycol, further aminated tetraethylene glycol diamine bottoms products from the reductive amination of tetraethylene glycol, and mixtures thereof.

9. The fatty acid amide surfactant composition of claim 1 wherein the said compound is selected from the group consisting of dicarboxylic acids and esters thereof having the formula:

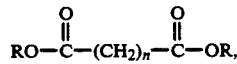

wherein R is hydrogen or alkyl of from 1 to 5 carbon atoms and n ranges from 0 to 8.

10. The fatty acid amide surfactant composition of claim 9 wherein the said compound is adipic acid.

11. The fatty acid amide surfactant composition of claim 1 wherein the said component is coconut acid.

12. The fatty acid amide surfactant composition of claim 1 wherein the said component is tallow acid.

13. The fatty acid amide surfactant composition of claim 1 wherein the said reaction is conducted in the temperature range of about 100° to about 250° C. and at a pressure ranging from about atmospheric to about 200 psig.

14. A process for preparing a water-soluble fatty acid amide surfactant composition comprising reacting together at least one compound selected from the group consisting of dicarboxylic acids and esters thereof; at least one alkylene glycol diamine bottoms product; and at least one component selected from the group consisting of fatty acids and esters thereof selected from the formula consisting of RCOOH wherein R is a linear or branched alkyl, alicyclic or alkylene group of from about 7 to 23 carbon atoms and R'COOR" wherein R' and R" are alkyl groups having a R'+R" sum of from about 7 to 23 carbon atoms, and wherein the alkylene glycol diamine bottoms product comprises at least one unreacted secondary amine —NH— moiety which exists following amide formation, wherein said compound ranges from about 5 to about 30 percent by weight based on the weight of the alkylene glycol diamine bottoms product and said component ranges from about 20 to about 85 percent by weight based on the weight of the alkylene glycol diamine bottoms product.

15. The process of claim 14 wherein the said compound is selected from the group consisting of dicarboxylic acids and esters thereof having the formula:

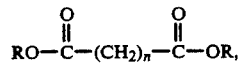

wherein R is hydrogen or alkyl of from 1 to 5 carbon atoms and n ranges from 0 to 8.

16. The process of claim 14 wherein the said alkylene glycol diamine bottoms product is selected from the group consisting of triethylene glycol diamine bottoms products from the reductive amination of triethylene glycol, further aminated triethylene glycol diamine bottoms products from the reductive amination of triethylene glycol, tetraethylene glycol diamine bottoms products from the reductive amination of tetraethylene glycol, further aminated tetraethylene glycol diamine bottoms products from the reductive amination of tetraethylene glycol and mixtures thereof.

17. The process of claim 14 wherein the said composition is molded or shaped into a surfactant bar.

18. A water-soluble fatty acid amide surfactant composition prepared by a process comprising:
   (a) reacting at least one compound selected from the group consisting of dicarboxylic acids and esters thereof with at least one polyoxyalkyleneamine residue comprising at least one unreacted secondary amine —NH— moiety which exists following amide formation to form the condensation product thereof, and
   (b) reacting said condensation product with at least one component selected from the group consisting of fatty acids and esters thereof selected from the formula consisting of RCOOH wherein R is a linear or branched alkyl, alicyclic or alkylene group of from about 7 to 23 carbon atoms and R'COOR" wherein R' and R" are alkyl groups having a R'+R" sum of from about 7 to 23 carbon atoms to form the fatty acid amide surfactant composition.

19. The fatty acid amide surfactant composition of claim 18 wherein the said polyoxyalkyleneamine residue is an alkylene glycol diamine bottoms product.

20. The fatty acid amide surfactant composition of claim 18 wherein the said polyoxyalkyleneamine residue is an ethylene glycol diamine bottoms product.

21. The fatty acid amide surfactant composition of claim 18 wherein the said polyoxyalkyleneamine residue is selected from the group consisting of triethylene glycol diamine bottoms products, further aminated triethylene glycol diamine bottoms products, tetraethylene glycol diamine bottoms products, further aminated tetraethylene glycol bottoms products, and mixtures thereof.

22. The fatty acid amide surfactant composition of claim 21 wherein the said polyoxyalkyleneamine residue is a triethylene glycol diamine bottoms product.

23. The fatty acid amide surfactant composition of claim 21 wherein the said polyoxyalkyleneamine residue is a tetraethylene glycol diamine bottoms product.

24. The fatty acid amide surfactant composition of claim 21 wherein the said polyoxyalkyleneamine residue is a further aminated triethylene glycol diamine bottoms product.

25. The fatty acid amide surfactant composition of claim 18 wherein the said polyoxyalkyleneamine residue is selected from the group consisting of triethylene glycol diamine bottoms products from the reductive amination on triethylene glycol, further aminated triethylene glycol diamine bottoms products from the reductive amination of triethylene glycol, tetraethylene glycol diamine bottoms products from the reductive amination of tetraethylene glycol, further aminated tetraethylene glycol diamine bottoms products from the reductive amination of tetraethylene glycol, and mixtures thereof.

26. The fatty acid amide surfactant composition of claim 18 wherein the said compound is selected from the group consisting of dicarboxylic acids and esters thereof of the formula:

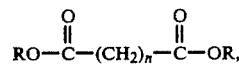

wherein R is hydrogen or alkyl of from 1 to 5 carbon atoms and n ranges from 0 to 8.

27. The fatty acid amide surfactant composition of claim 26 wherein the said compound is adipic acid.

28. The fatty acid amide surfactant composition of claim 26 wherein the said compound is glutaric acid.

29. The fatty acid amide surfactant composition of claim 26 wherein the said compound is diethyl oxalate.

30. The fatty acid amide surfactant composition of claim 18 wherein the said component is coconut acid.

31. The fatty acid amide surfactant composition of claim 18 wherein the said component is tallow acid.

32. The fatty acid amide surfactant composition of claim 18 wherein the reaction in steps (a) and (b) is conducted in the temperature range of from about 100° to about 250° C. and at a pressure ranging from atmospheric to about 200 psig.

33. A process for preparing a water-soluble fatty acid amide surfactant composition comprising:
   (a) reacting at least one compound selected from the group consisting of dicarboxylic acids and esters thereof with at least one alkylene glycol diamine bottoms product comprising at least one unreacted secondary amine —NH— moiety which exists following amide formation to form the condensation product thereof, and
   (b) reacting said condensation product with at least one component selected from the group consisting of fatty acids and esters thereof selected from the formula consisting of RCOOH wherein R is a linear or branched alkyl, alicyclic or alkylene group of from about 7 to 23 carbon atoms and R'COOR" wherein R' and R" are alkyl groups having a R'+R" sum of from about 7 to 23 carbon atoms to form the fatty acid amide surfactant composition.

34. The process of claim 33 wherein the said compound is selected from the group consisting of dicarboxylic acids and esters thereof having the formula:

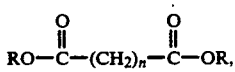

wherein R is hydrogen or alkyl of from 1 to 5 carbon atoms and n ranges from 0 to 8.

35. The process of claim 33 wherein the said alkylene glycol diamine bottoms product is selected from the group consisting of triethylene glycol diamine bottoms products from the reductive amination of triethylene glycol, further aminated triethylene glycol diamine bottoms products from the reductive amination of triethylene glycol, tetraethylene glycol diamine bottoms products from the reductive amination of tetraethylene glycol, further aminated tetraethylene glycol diamine bottoms products from the reductive amination of tetraethylene glycol and mixtures thereof.

36. The process of claim 33 wherein the said composition is molded or shaped into a surfactant bar.

37. The fatty acid amide surfactant composition of claim 4 wherein the said compound is selected from the group consisting of dicarboxylic acids and esters thereof having the formula:

$$RO-\overset{O}{\underset{\|}{C}}-(CH_2)_n-\overset{O}{\underset{\|}{C}}-OR,$$

wherein R is hydrogen or alkyl of from 1 to 5 carbon atoms and n ranges from 0 to 8 and wherein the said component is selected from the group consisting of fatty acids and esters thereof having 7 to 23 carbon atoms.

38. The fatty acid amide surfactant composition of claim 37 wherein the said component is a fatty acid ester.

39. The fatty acid amide surfactant composition of claim 21 wherein the said compound is selected from the group consisting of dicarboxylic acids and esters thereof of the formula:

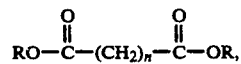

wherein R is hydrogen alkyl of from 1 to 5 carbon atoms and n ranges from 0 to 8 and the said component is selected from the group consisting of fatty acids and esters thereof having about 7 to about 23 carbon atoms.

40. The fatty acid amide surfactant composition of claim 39 wherein the component is a fatty acid ester.

* * * * *